(12) United States Patent
Murakoshi

(10) Patent No.: US 9,389,206 B2
(45) Date of Patent: Jul. 12, 2016

(54) ULTRASONIC TESTING METHOD AND ULTRASONIC ARRAY PROBE

(75) Inventor: Hitoshi Murakoshi, Osaka (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 311 days.

(21) Appl. No.: 14/128,661

(22) PCT Filed: Jun. 5, 2012

(86) PCT No.: PCT/JP2012/064434
§ 371 (c)(1),
(2), (4) Date: Mar. 10, 2014

(87) PCT Pub. No.: WO2012/176613
PCT Pub. Date: Dec. 27, 2012

(65) Prior Publication Data
US 2014/0202250 A1    Jul. 24, 2014

(30) Foreign Application Priority Data

Jun. 22, 2011  (JP) .................. 2011-138535

(51) Int. Cl.
| | | |
|---|---|---|
| *G01N 29/04* | (2006.01) | |
| *G01N 29/24* | (2006.01) | |
| *G01N 29/22* | (2006.01) | |
| *G01N 29/32* | (2006.01) | |
| *G01N 29/07* | (2006.01) | |

(52) U.S. Cl.
CPC ............. *G01N 29/24* (2013.01); *G01N 29/04* (2013.01); *G01N 29/041* (2013.01); *G01N 29/07* (2013.01); *G01N 29/221* (2013.01); *G01N 29/223* (2013.01); *G01N 29/2456* (2013.01); *G01N 29/32* (2013.01); *G01N 2291/106* (2013.01)

(58) Field of Classification Search
CPC ..... G01N 29/04; G01N 29/24; G01N 29/041; G01N 29/223; G01N 29/2456; G01N 29/07; G01N 29/221; G01N 29/32; G01N 2291/106
USPC ........................................................... 73/632
See application file for complete search history.

(56) References Cited

U.S. PATENT DOCUMENTS

| 2,320,947 A | * | 6/1943 | Martin | .................... | F16B 31/04 |
| | | | | | 174/138 R |
| 5,786,535 A | * | 7/1998 | Takeuchi | ............. | G01N 29/043 |
| | | | | | 73/619 |
| 9,091,638 B2 | * | 7/2015 | Frederick | ............... | G01N 29/07 |

FOREIGN PATENT DOCUMENTS

| JP | 8-173433 | 7/1996 |
| JP | 10-62396 | 3/1998 |
| JP | 11-206764 | 8/1999 |
| JP | 2001-104304 | 4/2001 |
| JP | 2003-004709 | 1/2003 |
| WO | 2010/101104 | 9/2010 |

* cited by examiner

*Primary Examiner* — J M Saint Surin
(74) *Attorney, Agent, or Firm* — Clark & Brody

(57) ABSTRACT

An array probe 3 is provided with an array probe body 32 having a plurality of transducers 31 linearly arranged. The array probe is provided with a vibration insulating member 4 that is installed onto a transducer surface 33 to absorb the vibrations of the transducer surface, and an installation frame 5 for installing the vibration insulating member. The vibration insulating member has an opening part 41, and the width dimension of the opening part is smaller than the width dimension of the transducer surface. By installing the vibration insulating member having the opening width dimension corresponding to the distance from a test object surface of a target flaw onto the transducer surface, ultrasonic testing is performed, whereby even for a flaw near the surface, flaw echo is made less liable to be buried in surface echo, and the flaw can be detected easily.

2 Claims, 8 Drawing Sheets

80% Sensitivity

| Distance from Surface to Flaw (mm) | Opening Width Dimension (mm) | | | | | | | |
|---|---|---|---|---|---|---|---|---|
| | 4.5 | 6 | 7 | 8 | 9 | 10 | 11 | 12.5 |
| 5 | 32 | 30 | 29.3 | 29.7 | 30.2 | 30.2 | 30.9 | 32.2 |
| 10 | 34.9 | 32.2 | 30.1 | 30 | 30.3 | 30.2 | 30.5 | 31.1 |
| 15 | 37.9 | 34.7 | 32 | 31.4 | 31.6 | 31.7 | 32.3 | 33.3 |
| 20 | 40 | 37.1 | 34.1 | 33.6 | 33.6 | 33.4 | 33.5 | 35.2 |

20%S Echo Distance

| Distance from Surface to Flaw (mm) | Opening Width Dimension (mm) | | | | | | | |
|---|---|---|---|---|---|---|---|---|
| | 4.5 | 6 | 7 | 8 | 9 | 10 | 11 | 12.5 |
| 5 | 6 | 4.5 | 6 | 6.4 | 6.6 | 7 | 7 | 9.2 |
| 10 | 6.8 | 6.4 | 6.5 | 6.5 | 8.8 | 8 | 7.8 | 9 |
| 15 | 8.5 | 8.5 | 8.5 | 8.5 | 9 | 8.6 | 8.6 | 11.6 |
| 20 | 11.5 | 11.8 | 11.5 | 11.5 | 11 | 8 | 11 | 12 |

ULTRASONIC TESTING METHOD AND ULTRASONIC ARRAY PROBE

TECHNICAL FIELD

The present invention relates to an ultrasonic testing method for performing flaw testing by using an ultrasonic array probe, and the ultrasonic array probe. More particularly, the invention relates to an ultrasonic testing method for facilitating detection of a flaw near a surface of a test object, and an ultrasonic array probe.

BACKGROUND ART

Conventionally, there has been known an ultrasonic testing method using an ultrasonic array probe in which transducers are linearly arranged to detect a flaw in a wheel such as a railway wheel.

Unfortunately, for a flaw existing near a surface of a test object, flaw echo is buried in surface echo, so that the detection of flaw may be difficult.

Also, there has been an ultrasonic testing method for detecting a flaw near a surface by controlling the beam diameter of the ultrasonic beam of an ultrasonic array probe so that the beam diameter (d) and the in-water wavelength ($\lambda_0$) of ultrasonic beam are $1/(d \cdot \lambda_0) \geq 1$ (for example, refer to Patent Literature 1) to enhance the defect detectability (S/N). Unfortunately, also in such a method, for a flaw existing near a surface, flaw echo is buried in surface echo, so that the flaw may not be detected sufficiently.

CITATION LIST

Patent Literature

[Patent Literature 1] JP2003-4709A

SUMMARY OF INVENTION

Technical Problem

The present invention has been made to solve the above-described problems with the prior arts, and an object thereof is to provide an ultrasonic testing method and an ultrasonic array probe capable of facilitating detection of a flaw existing near a surface of a test object.

Solution to Problem

The present inventor conducted studies earnestly and obtained a finding that by installing a vibration insulating member having the configuration described below onto a transducer surface, the range of distance from the surface of test object in which surface echo appears is made narrow, and also the intensity of flaw echo is changed. Hereunder, this finding will be explained.

The vibration insulating member was installed onto the transducer surface as described below.

The vibration insulating member has an opening part, and the dimension of the width of opening part (hereinafter, referred also to as an opening part width) is smaller than the width dimension of the transducer surface. The vibration insulating member absorbs the vibrations of the transducer surface. Herein, the width of opening part refers to the size of opening part in the direction perpendicular to the arrangement direction of transducers in the state in which the vibration insulating member has been installed onto the transducer surface. Also, the width of transducer surface refers to the size of the transducer surface in the direction perpendicular to the arrangement direction of transducers.

The vibration insulating member was installed so as to come into contact with the transducer surface of an ultrasonic array probe (hereinafter, referred also to as an array probe).

In the state in which the vibration insulating member has been installed, a part in the width direction of transducer surface is exposed through the opening part. A portion exposed by the opening part of the transducer surface as described above is referred to as an exposed surface. Since the width of opening part is narrower than the width of transducer surface, the width of exposed surface is narrower than the width of the transducer surface.

In the state in which the vibration insulating member had been installed onto the transducer surface, the vibration insulating member absorbed the vibrations of a region with which the vibration insulating member is in contact in the transducer surface.

FIG. 1 is a schematic diagram showing the distributions of propagation time of surface echo in the case where the above-described vibration insulating member has been installed onto a transducer surface and in the case where the vibration insulating member has not been installed onto the transducer surface. The abscissas represent propagation time, and the ordinates represent the ratio of surface echo at each propagation time.

The distribution of propagation time of surface echo in the case where the vibration insulating member has been installed onto the transducer surface is narrowed to the short time side as compared with the case where the vibration insulating member has not been installed.

The main reason why the distribution of propagation time of surface echo in the case where the vibration insulating member has been installed onto the transducer surface is narrowed to the short time side as described above as compared with the case where the vibration insulating member has not been installed is thought to be as described below.

FIGS. 2A and 2B are schematic views showing propagation paths of ultrasonic waves reflected by a surface of a test object, which are viewed from the transducer arrangement direction. FIG. 2A is a schematic view showing propagation paths in the case where a vibration insulating member has not been installed onto a transducer surface, and FIG. 2B is a schematic view showing propagation paths in the case where the vibration insulating member has been installed onto the transducer surface.

The length of a propagation path E through which the ultrasonic waves transmitted from a transducer surface 111 of an array probe 101 perpendicularly to a surface 121 of a test object 102 are reflected perpendicularly by the surface 121 and return to the transducer surface 111 is the same in the case where a vibration insulating member 103 has not been installed and in the case where the vibration insulating member 103 has been installed.

However, as the propagation path through which the ultrasonic waves transmitted from a transducer surface 111 perpendicularly to the surface 121 of the test object 102 are reflected by the surface 121 and return to the transducer surface 111, for example, in the case where the vibration insulating member 103 has not been installed, there is present a propagation path E1 through which the ultrasonic waves transmitted from one end side in the width direction of the transducer surface 111 returns to the other end side in the width direction of the transducer surface 111. This propagation path E1 is longer than a propagation path E2 through which the ultrasonic waves transmitted from one end side in the width direction of an exposed surface 112 returns to the other end side in the width direction of the exposed surface 112 in the case where the vibration insulating member 103 has been installed.

Therefore, the distribution of propagation distance through which the ultrasonic waves transmitted from the transducer surface 111 are reflected by the surface 121 of the test object and return to the transducer surface 111 in the case where the vibration insulating member 103 has been installed is narrowed to the short distance side as compared with the case where the vibration insulating member 103 has not been installed.

Thus, the distribution of propagation time in the case where the vibration insulating member 103 has been installed is narrowed to the short time side as compared with the case where the vibration insulating member 103 has not been installed.

In other words, the range of distance from the test object surface in which surface echo appears in the case where the vibration insulating member 103 has been installed becomes easily narrower than that in the case where the vibration insulating member 103 has not been installed.

Next, the change in the intensity of flaw echo produced by the installation of the vibration insulating member onto the transducer surface will be explained.

The present inventor obtained a finding that the intensity of flaw echo changes depending on the opening width dimension of the vibration insulating member, and the intensity becomes at a peak at a certain opening width dimension.

The reason for this is thought to be as described below. The short distance sound field limit distance of transducer, in other words, the distance from the transducer at which the sound pressure of ultrasonic waves becomes at a maximum changes depending on the diameter of transducer in such a manner as being expressed by the publicly-known formula ($X_0 = D^2/4\lambda$, $X_0$: short distance sound field limit distance, D: diameter of transducer, $\lambda$: wavelength in medium) in the case where the transducer is a circular transducer. For the array probe onto which the vibration insulating member is installed, it is thought that the short distance sound field limit distance changes depending on the width of exposed surface contributing to vibrations in the transducer surface, that is, the opening width dimension. Therefore, it is thought that the intensity of flaw echo becomes at a peak when the distance from the test object surface to a flaw in the test object and the short distance sound field limit distance at the opening width dimension of the installed vibration insulating member agree with each other.

The present inventor obtained a finding that by installing the vibration insulating member having the opening part whose width is narrower than the width of the transducer surface so as to be in contact with the transducer surface as described above, vibrations of a region with which the vibration insulating member is in contact in the transducer surface are absorbed, and by narrowing the vibrating region to the exposed surface having a width narrower than the width of the transducer surface, the range of distance from the test object surface in which surface echo appears is made narrower than the range in the case where the vibration insulating member has not been installed. Also, the present inventor obtained a finding that the intensity of flaw echo changes depending on the opening width dimension of the vibration insulating member, and the intensity becomes at a peak at a certain opening width dimension.

Considering both of the range of distance from the test object surface in which surface echo appears in the case where the vibration insulating member has been installed and the intensity of flaw echo, the opening width dimension of vibration insulating member at which a flaw is easily detected is determined in advance according to the distance from the test object surface to a target flaw. In ultrasonic testing, the ultrasonic testing is performed by installing the vibration insulating member having an opening width dimension corresponding to the distance from the test object surface to the target flaw onto the transducer surface. From this fact, the present inventor found that even for a flaw near the surface, flaw echo is less liable to be buried in surface echo, and the flaw can be detected easily.

The present invention has been accomplished based on the above finding by the present inventors. That is, in order to solve the above-described problems, the present invention provides an ultrasonic testing method comprising a step of performing ultrasonic testing by detachably installing a vibration insulating member, which has an opening part whose width is narrower than the width of a transducer surface of an ultrasonic probe body having transducers linearly arranged and absorbs the vibrations of the transducer surface, onto the transducer surface so that a part in the width direction of the transducer surface is exposed through the opening part and the non-exposed part of the transducer surface is in contact with the vibration insulating member, and by radiating ultrasonic waves from the transducer surface onto a surface of a test object, wherein the width dimension of the opening part is determined in advance according to the distance from the surface of the test object to a target flaw positioned near the surface of the test object.

According to the present invention, by installing the vibration insulating member having the opening part whose width is narrower than the width of the transducer surface, the vibrations of the region that is in contact with the vibration insulating member in the transducer surface are absorbed, and the vibrating region is narrowed to the exposed surface having a width narrower than the width of the transducer surface. That is, by the vibration insulating member, the width of vibrating region is narrowed from the width of the transducer surface to the width of the exposed surface. Since the width of the exposed surface is narrower than the width of the transducer surface, the range of distance from the test object surface in which surface echo appears becomes narrower than that in the case where the vibration insulating member has not been installed.

The opening width dimension corresponding to the distance from the test object surface to the target flaw is determined in advance, and when ultrasonic testing is performed, the ultrasonic testing is performed by installing the vibration insulating member having an opening width dimension corresponding to the distance from the test object surface to the target flaw.

When the opening width dimension corresponding to the distance from the test object surface to the target flaw is determined, for ease of detection of the target flaw, the opening width dimension corresponding to the distance from the test object surface to the target flaw is determined in consideration of both of the range of distance from the test object surface in which surface echo appears and the intensity of flaw echo. Thereby, even for a flaw near the surface, flaw echo is made less liable to be buried in surface echo, and the flaw can be detected easily.

In order to determine the opening width dimension corresponding to the distance from the test object surface to the target flaw so as to facilitate detection of the target flaw, for example, the following procedure has only to be carried out.

A specimen provided with a plurality of artificial flaws each having a different distance from the test object surface and a plurality of vibration insulating members each having a different opening width dimension are prepared, ultrasonic testing is performed by changing the plurality of vibration insulating members each having a different opening width dimension for individual artificial flaws, and the range of distance from the test object surface in which surface echo appears and the intensity of flaw echo of artificial flaw are examined. Thus, the range of distance from the test object surface in which surface echo appears for each distance from the test object surface to an artificial flaw and for each opening width dimension of the vibration insulating member and the data on the intensity of flaw echo of artificial flaw are gotten together.

Based on the range of distance from the test object surface in which surface echo appears and the intensity of flaw echo of artificial flaw, the opening width dimension at which a flaw is easily detected is determined for each distance from the test object surface to the target flaw. In other words, the opening width dimension corresponding to the distance from the test object surface to the target flow is determined. In order to determine the opening width dimension, for example, in the case where the position of target flaw is close to the test object surface, the opening width dimension such that the range of distance from the test object surface in which surface echo appears becomes approximately the narrowest has only to be determined, and in the case where the position of target flaw is far from the test object surface, the opening width dimension such that the intensity of flaw echo of the target flaw becomes approximately the highest has only to be determined.

Also, in order to determine the opening width dimension corresponding to the distance from the test object surface to the target flaw, the opening width dimension may be determined so that the range of distance from the test object surface in which surface echo appears becomes approximately the narrowest over the whole distance, or the opening width dimension may be determined so that the intensity of flaw echo of the target flaw becomes approximately the highest.

Thus, by performing ultrasonic testing by installing the vibration insulating member having the opening width dimension corresponding to the distance from the test object surface to the target flaw onto the transducer surface, even for a flaw near the surface, flaw echo is made less liable to be buried in surface echo, and the flaw can be detected easily.

Also, since the vibration insulating member is detachable from the transducer surface, the vibration insulating member can be exchanged. Therefore, even in the case where the distances from the test object surface to the plurality of target flaws are different, the vibration insulating member having the opening width dimension corresponding to the distance from the test object surface to each target flaw is selected and installed onto the array probe body, whereby a flaw can be detected by using a single array probe.

In order to solve the above-described problems, the present invention also provides an ultrasonic array probe comprising: an ultrasonic array probe body having transducers linearly arranged; and a vibration insulating member for absorbing vibrations of a transducer surface, which member has an opening part whose width is narrower than the width of the transducer surface of the ultrasonic array probe body, and is detachably installed onto the transducer surface so that a part in the width direction of the transducer surface of the ultrasonic array probe body is exposed through the opening part and the non-exposed part of the transducer surface is in contact with the vibration insulating member, wherein the width dimension of the opening part is determined in advance according to the distance from the surface of the test object to a target flaw positioned near the surface of the test object.

Advantageous Effect of Invention

According to the present invention, a flaw near the surface of test object can be detected easily.

BRIEF DESCRIPTION OF DRAWINGS

FIG. 2A is a schematic view showing propagation paths in the case where a vibration insulating member has not been installed onto a transducer surface, and FIG. 2B is a schematic view showing propagation paths in the case where the vibration insulating member has been installed onto the transducer surface.

FIG. 4A is a perspective view of the array probe, FIG. 4B is an exploded perspective view of the array probe, FIG. 4C is a front view of the array probe, which is viewed from the normal direction of a transducer surface of the array probe, and FIG. 4D is a plan view of the array probe.

FIG. 9A is a data table of 80% sensitivity, and FIG. 9B is a graph of 80% sensitivity.

FIG. 10A is a data table of 20% S echo distance, and FIG. 10B is a graph of 20% S echo distance.

DESCRIPTION OF EMBODIMENT

The ultrasonic testing method in accordance with an embodiment of the present invention will now be described with reference to the accompanied drawings as appropriate.

Figure 1:
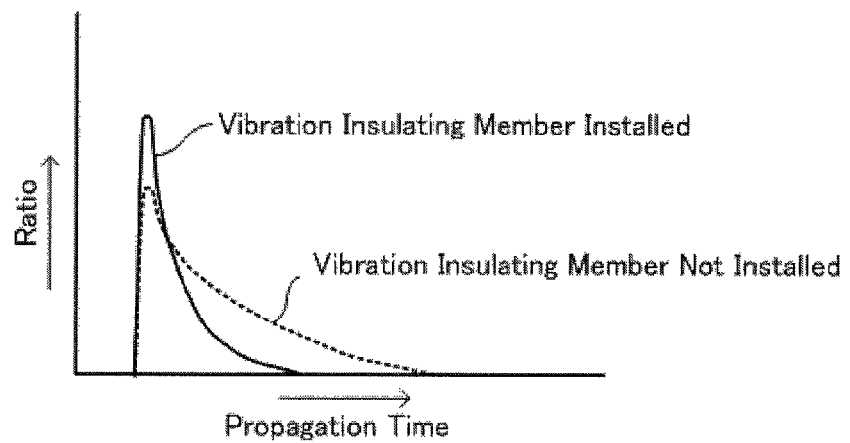
FIG. 1 is a schematic diagram showing the distributions of propagation time of surface echo in the case where a vibration insulating member has been installed onto a transducer surface and in the case where the vibration insulating member has not been installed onto the transducer surface.
Figure 2A:
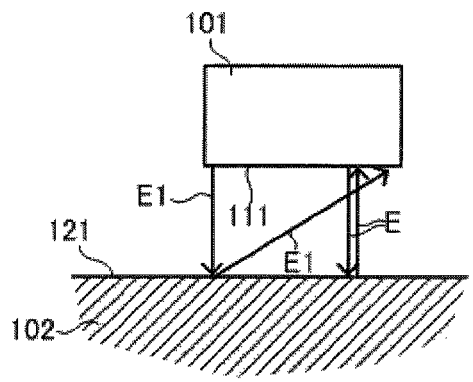
FIGS. 2A and 2B are schematic views showing propagation paths of ultrasonic waves reflected by a surface of a test object, which are viewed from the transducer arrangement direction.
Figure 2B:
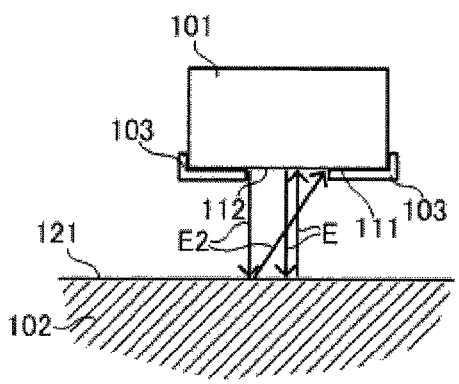
Figure 3:
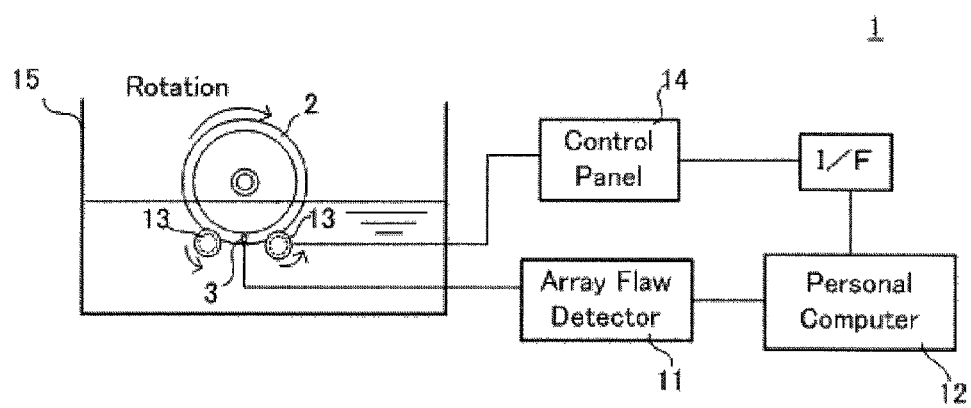
FIG. 3 is a configuration diagram for explaining one example of an ultrasonic testing apparatus used for the ultrasonic testing method in accordance with an embodiment of the present invention.

FIG. 3 is a configuration diagram for explaining one example of an ultrasonic testing apparatus used for the ultrasonic testing method in accordance with this embodiment.

An ultrasonic testing apparatus 1 is provided with an ultrasonic array probe (hereinafter, referred also to as an array probe) 3 for testing a wheel 2. The array probe 3 is arranged so as to face a tested portion of the wheel 2.

Also, the ultrasonic testing apparatus 1 is provided with an array flaw detector 11 performing functions of transmitting a transmission/reception control signal to the array probe 3, amplifying the signal received from the array probe 3, and the like; a personal computer 12 performing functions of setting various parameters for the array flaw detector 11, preparing images of an A scope, a B scope, and the like by receiving a signal from the array flaw detector 11, and the like; a control panel 14 for giving a rotation signal and the like to a rotary driving section 13, described later; the rotary driving section 13 for rotating the wheel 2 to perform testing on the entire circumference of the wheel 2; and a tank 15 for immersing the wheel 2 and the array probe 3 in water.

Figure 4A:
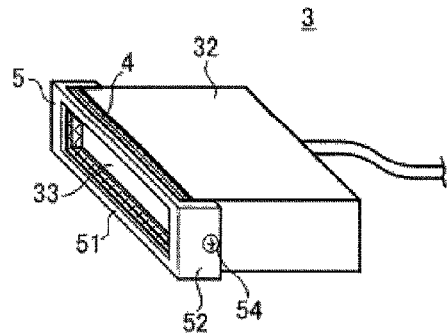
FIGS. 4A to 4D are views showing the configuration of an array probe.
Figure 4B:
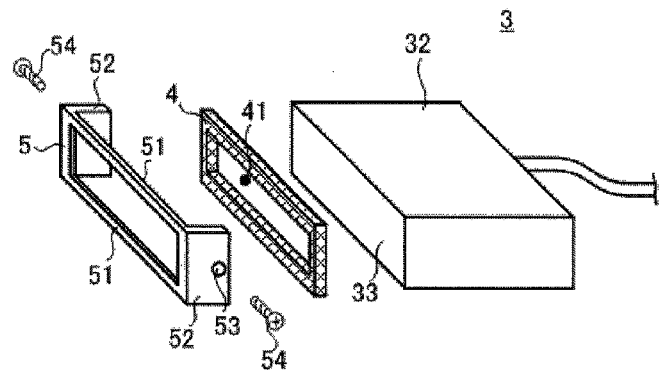
Figure 4C:
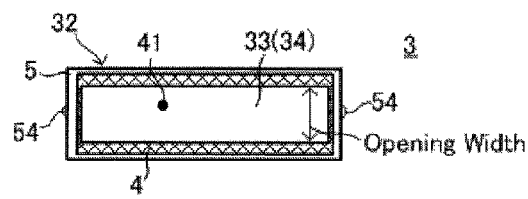
Figure 4D:
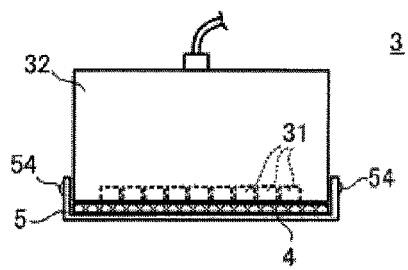

FIGS. 4A to 4D are views showing the configuration of the array probe 3. FIG. 4A is a perspective view of the array probe 3, FIG. 4B is an exploded perspective view of the array probe 3, FIG. 4C is a front view of the array probe 3, which is viewed from the normal direction of a transducer surface of the array probe 3, and FIG. 4D is a plan view of the array probe 3.

The array probe 3 is provided with an ultrasonic array probe body (hereinafter, referred also to as an array probe body) 32 having a plurality of transducers 31 linearly arranged. The surface of the array probe body 32 for transmitting ultrasonic waves from the transducers 31 is referred to as a transducer surface 33.

The array probe 3 is provided with a vibration insulating member 4 that is installed onto the transducer surface 33 to absorb the vibrations of the transducer surface 33, and an installation frame 5 for installing the vibration insulating member 4.

The material of the vibration insulating member 4 is, for example, rubber, resin, or cork; however, it may be any material that absorbs the vibrations of the transducer surface 33.

The vibration insulating member 4 has an opening part 41, and the width dimension of the opening part 41 is smaller than the width dimension of the transducer surface 33. The opening part 41 has a rectangular shape extending in the arrangement direction of the transducers 31. The width of the opening part 41 refers to the size of the opening part 41 in the direction perpendicular to the arrangement direction of transducers 31 in the state in which the vibration insulating member 4 has been installed onto the transducer surface 33. Also, the width of the transducer surface 33 refers to the size of the transducer surface in the direction perpendicular to the arrangement direction of transducers 31.

The vibration insulating member 4 is installed by using the installation frame 5 so as to be in contact with the transducer surface 33.

In the state in which the vibration insulating member 4 has been installed, a part in the width direction of the transducer surface 33 is exposed through the opening part 41. A portion exposed by the opening part 41 of the transducer surface as described above is referred to as an exposed surface 34. Since the width of the opening part 41 is narrower than the width of the transducer surface, the width of the exposed surface 34 is narrower than the width of the transducer surface.

In the state of having been installed onto the transducer surface 33, the vibration insulating member 4 absorbs the vibrations of the region with which the vibration insulating member 4 is in contact in the transducer surface 33.

The installation frame 5 is provided with fixing parts 51 for fixing the vibration insulating member 4 to the transducer surface 33, and side surface parts 52 butting against the side surfaces of the array probe body 32, the side surfaces being perpendicular to the transducer arrangement direction, and in each of the side surface parts 52, a threaded hole 53 penetrating the side surface part 52 is provided.

In order to install the vibration insulating member 4 onto the transducer surface 33, the vibration insulating member 4 is disposed so as to be in contact with the transducer surface 33, and the vibration insulating member 4 is fixed to the transducer surface 33 by the fixing parts 51 of the installation frame 5. Then, screws 54 are screwed into the threaded holes 53 to mount the installation frame 5.

Thus, the vibration insulating member 4 is detachably installed onto the transducer surface 33.

The ultrasonic testing method is carried out as described below.

The vibration insulating member 4 having the opening width dimension corresponding to the distance from the test object surface to the target flaw is installed onto the transducer surface 33 of the array probe body 32 by using the installation frame 5.

Then, the array probe 3 is disposed so that the transducer surface 33 faces the tested portion of the wheel 2, and water, which serves as a coupling medium, is put into the tank 15 so that the wheel 2 and the array probe 3 are immersed. As the coupling medium, oil or the like can also be used. From the personal computer 12, the testing conditions such as the intensity of ultrasonic waves transmitted from the array probe 3 and the scanning speed are transmitted to the array flaw detector 11, and the testing conditions are converted into the transmission/reception control signal by the array flaw detector 11 and are transmitted to the array probe 3. The array probe 3 transmits ultrasonic waves to the tested portion of the wheel 2, receives reflection echo, and transmits the signal corresponding to the received reflection echo to the array flaw detector 11. The array flaw detector 11 amplifies the signal received from the array probe 3 and transmits it to the personal computer 12. The personal computer 12 displays the image of A scope, B scope, or the like. Also, a rotation signal is transmitted from the personal computer 12 to the rotary driving section 13 via the control panel 14, whereby the wheel 2 is rotated, so that the entire circumference of the wheel 2 can be tested. By doing this, the flaw detection of the wheel 2 can be carried out. Thus, the ultrasonic testing method includes a step of performing ultrasonic testing by installing the vibration insulating member 4 having the opening width dimension corresponding to the distance from the test object surface to the target flaw onto the transducer surface 33 of the array probe body 32 and by radiating ultrasonic waves from the transducer surface 33 onto the surface of test object.

The transmission and reception of ultrasonic waves from the array probe 3 are accomplished, for example, by a linear scan or a steering scan. The linear scan is a method in which some transducers 31 constituting the array probe 3 are made one transmission unit; when ultrasonic waves are transmitted in the one transmission unit, the ultrasonic waves are transmitted so that the ultrasonic waves sent from each transducer 31 are in parallel with each other, or so that the ultrasonic waves sent from each transducer 31 are concentrated on one point by shifting the timing of transmission of each transducer 31; and in this state, the ultrasonic waves are parallel-scanned by controlling the array probe 3 by using the transmission/reception control signal sent from the array flaw detector 4 so that the transmission unit is shifted successively along the arrangement direction of the transducer 31. The steering scan is a method in which some transducers 31 constituting the array probe 3 are made one transmission unit; when ultrasonic waves are transmitted in the one transmission unit, the ultrasonic waves are transmitted so that the ultrasonic waves sent from each transducer 31 are in parallel with each other, or so that the ultrasonic waves sent from each transducer 31 are concentrated on one point by shifting the timing of transmission of each transducer 31; and in this state, scanning is performed by changing the exit angle.

Next, the installation of the vibration insulating member 4 onto the transducer surface 33, which is a feature of this embodiment, will be explained.

Figure 5:
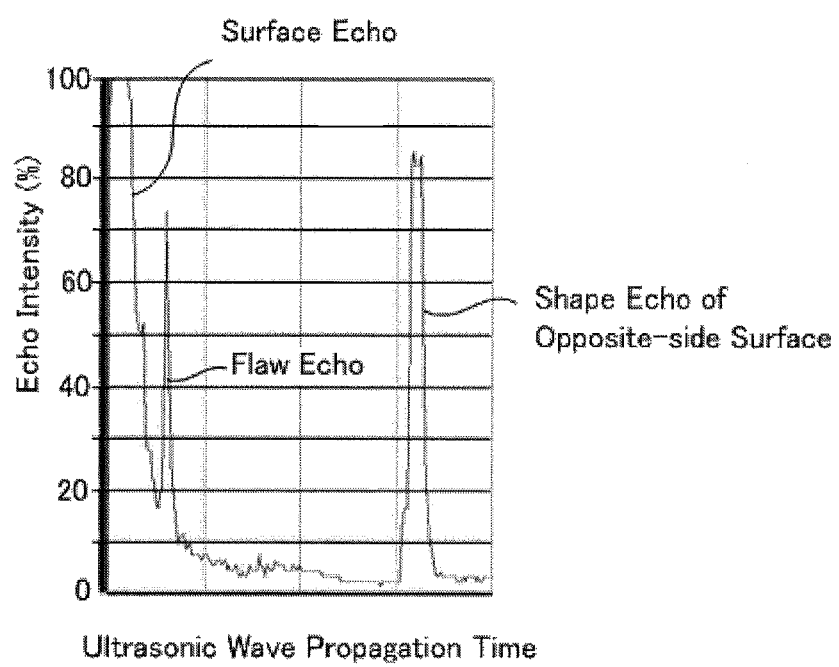
FIG. 5 is a diagram showing an A scope at the time when ultrasonic testing is performed on a test object provided with an artificial flaw.

FIG. 5 is a diagram showing an A scope at the time when ultrasonic testing is performed on a test object provided with an artificial flaw. The abscissas represent propagation time of ultrasonic waves, showing the distance from the surface of test object, and the ordinates represent the intensity of echo.

The test object for which this A scope has been picked up is provided with an artificial flaw formed perpendicularly toward the incident surface which ultrasonic waves enter from the surface on the opposite side of the incident surface. The flaw echo of the front end of artificial flaw is detected by the A scope. Also, on the A scope, the surface echo of the incident surface and the shape echo of the surface on the opposite side of the incident surface appear.

The surface echo appears from the position of the surface of test object, and decreases as the distance from the test object surface increases. In the case where a flaw is present near the surface of test object, and the intensity of flaw echo is low, the flaw echo is buried in the surface echo, and the flaw cannot be detected.

Therefore, it is desirable that the range of distance from the test object surface in which surface echo appears is as narrow as possible, and it is desirable that flaw echo appears so that the intensity thereof is as high as possible.

In this embodiment, by installing the vibration insulating member 4 onto the transducer surface 33 to decrease the width dimension of the exposed surface 34, the range of distance from the test object surface in which surface echo appears is made narrow, and by changing the intensity of flaw echo, a flaw is made easy to detect.

Specifically, the opening width dimension of vibration insulating member at which a flaw is easily detected is determined in advance according to the distance from the test object surface to the target flaw, and when ultrasonic testing is performed, the ultrasonic testing is performed by installing the vibration insulating member having an opening width dimension corresponding to the distance from the test object surface to the target flaw.

In the case where the opening width dimension corresponding to the distance from the test object surface to the target flaw, if the opening width dimension is determined according to the distance from the test object surface to the target flaw considering both of the range of distance from the test object surface in which surface echo appears and the intensity of flaw echo so that the target flaw can be detected easily, even for a flaw near the surface, flaw echo is less liable to be buried in surface echo, and the flaw can be detected easily.

In order to determine the opening width dimension corresponding to the distance from the test object surface to the target flaw so that the target flaw can be detected easily, for example, the following procedure has only to be carried out.

A specimen provided with a plurality of artificial flaws each having a different distance from the test object surface and a plurality of vibration insulating members 4 each having a different opening width dimension are prepared, ultrasonic testing is performed by changing the plurality of vibration insulating members 4 each having a different opening width dimension for individual artificial flaws, and the range of distance from the test object surface in which surface echo appears and the intensity of flaw echo of artificial flaw are examined. Thus, the range of distance from the test object surface in which surface echo appears for each distance from the test object surface to an artificial flaw and for each opening width dimension of the vibration insulating member and the data on the intensity of flaw echo of artificial flaw are gotten together.

Based on the range of distance from the test object surface in which surface echo appears and the intensity of flaw echo of artificial flaw, the opening width dimension at which a flaw is easily detected is determined for each distance from the test object surface to the target flaw. In other words, the opening width dimension corresponding to the distance from the test object surface to the target flow is determined. In order to determine the opening width dimension, for example, in the case where the position of target flaw is close to the test object surface, the opening width dimension such that the range of distance from the test object surface in which surface echo appears becomes approximately the narrowest has only to be determined, and in the case where the position of target flaw is far from the test object surface, the opening width dimension such that the intensity of flaw echo of the target flaw becomes approximately the highest has only to be determined.

Also, in order to determine the opening width dimension corresponding to the distance from the test object surface to the target flaw, the opening width dimension may be determined so that the range of distance from the test object surface in which surface echo appears becomes approximately the narrowest over the whole distance, or the opening width dimension may be determined so that the intensity of flaw echo of the target flaw becomes approximately the highest.

Thus, by performing ultrasonic testing by installing the vibration insulating member 4 having the opening width dimension corresponding to the distance from the test object surface to the target flaw onto the transducer surface, even for a flaw near the surface, flaw echo is made less liable to be buried in surface echo, and the flaw can be detected easily.

In particular, this procedure is effective in detecting a flaw such that the distance from the test object surface is within 40 mm, and further this distance is within 10 mm.

Also, since the vibration insulating member is detachable from the transducer surface, the vibration insulating member can be exchanged. Therefore, even in the case where the distances from the test object surface to the plurality of target flaws are different, the vibration insulating member having the opening width dimension corresponding to the distance from the test object surface to each target flaw is selected and installed onto the array probe body, whereby a flaw can be detected by using a single array probe.

In the above-described embodiment, the shape of the opening part 41 has been made rectangular; however, the shape of the opening part 41 is not limited to a rectangular shape, and may be, for example, an oval shape or a trapezoidal shape.

Also, the shape of the vibration insulating member 4 is not limited to the above-described shape, and may be any shape such that the width dimension of the exposed surface 34 is made small.

For example, two columnar vibration insulating members extending in the arrangement direction of transducers 31 may be used.

Figure 6:
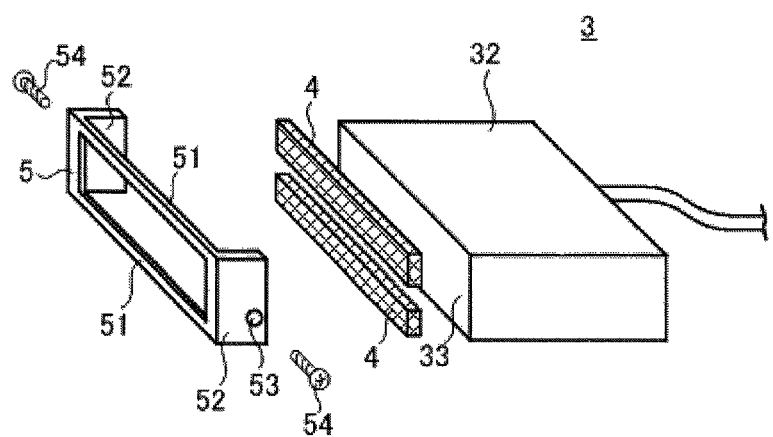
FIG. 6 is an exploded perspective view of an array probe using two columnar vibration insulating members.

FIG. 6 is an exploded perspective view of an array probe 3 using two columnar vibration insulating members.

The two columnar vibration insulating members 4a are arranged on both end sides in the width direction of the transducer surface 33, and are installed by the installation frame 5. The width of the exposed surface 34 in this case is the distance between the two vibration insulating members 4a.

Even in the case where such two columnar vibration insulating members 4a are installed, the effect same as that in the case where the vibration insulating member 4 having the opening part 41 is installed can be achieved.

Working Example

Next, a working example of ultrasonic testing method will be explained.

Ultrasonic testing was performed by using the ultrasonic testing apparatus 1 same as that shown in FIG. 3 and by mounting a test object for testing in place of the wheel 2.

In the testing, there was used the array probe body 32 in which one hundred and twenty-eight transducers 31 each having a length in the arrangement direction of 0.85 mm were linearly arranged at a pitch of 1 mm, and the width of the transducer surface 33 was 12.5 mm. The oscillation frequency of the transducer 31 was 5 MHz.

Seven foamed rubber-made vibration insulating members 4 each having an opening width of 4.5 mm, 6 mm, 7 mm, 8 mm, 9 mm, 10 mm, and 11 mm, respectively, were prepared, and ultrasonic testing was performed by installing each of these vibration insulating members 4 successively and exchangedly onto the transducer surface 33 of the array probe body 32 by using the installation frame 5. The thickness of the vibration insulating member 4 was set at 2 mm, and the length in the transducer arrangement direction of the opening part 41 was made longer than the arrangement length of the arranged transducers 31.

The ultrasonic testing was performed by a linear scan with one oscillation unit being 16.

As the array flaw detector 11, a portable phased array ultrasonic flaw detector "PAL2" manufactured by Japan Clout Kramer Co. Ltd. was used.

As the test object, an Fe stepped test specimen was used.

Figure 7:
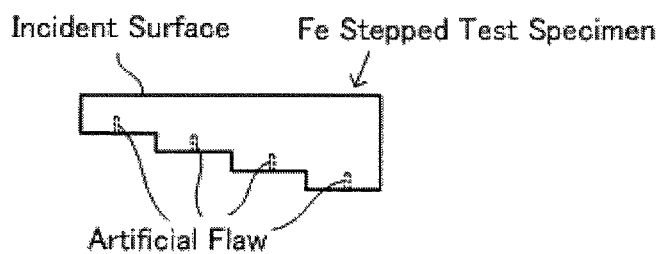
FIG. 7 is a construction view of an Fe stepped test specimen.

FIG. 7 is a construction view of the Fe stepped test specimen.

In the Fe stepped test specimen, artificial flaws each consisting of a 1.19 mm-diameter flat bottomed hole were formed perpendicularly toward the incident surface which ultrasonic waves enter from the surfaces on the opposite side of the incident surface. The distance from the incident surface to the front end of each artificial flaw was made of four steps of 5 mm, 10 mm, 15 mm, and 20 mm.

Figure 8:
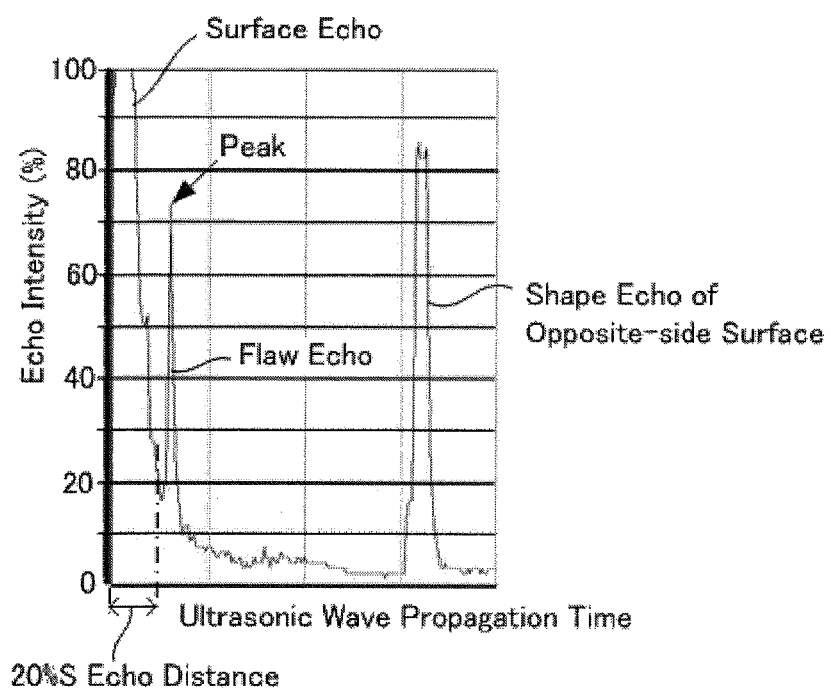
FIG. 8 is a diagram for explaining a method for evaluating the intensity of flaw echo and a method for evaluating the range of distance from a test object surface in which surface echo appears.

FIG. 8 is a diagram for explaining a method for evaluating the intensity of flaw echo and a method for evaluating the range of distance from a test object surface in which surface echo appears.

The intensity of flaw echo was evaluated as described below: the sensitivity of the array flaw detector 11 was controlled so that the peak intensity of flaw echo was 80% of full scale of the intensity on the A scope, and evaluation was done by the sensitivity (dB) at that time (hereinafter, this sensitivity is referred to as an 80% sensitivity). It is shown that as the value of 80% sensitivity decreases, the peak intensity of flaw echo appears greatly.

The range of distance from the test object surface in which surface echo appears was evaluated by the distance from the test object surface at the time when the intensity of surface echo at the time when the sensitivity of the array flaw detector 11 was controlled to the 80% sensitivity decreased to 20% of full scale of the intensity on the A scope (hereinafter, referred to as a 20% S echo distance).

In this working example, the range of distance from the test object surface in which surface echo appears was evaluated by controlling the sensitivity of array flaw detector to the 80% sensitivity; however, the evaluation may be done by making the sensitivity of array flaw detector the same.

Figures 9A, 9B:
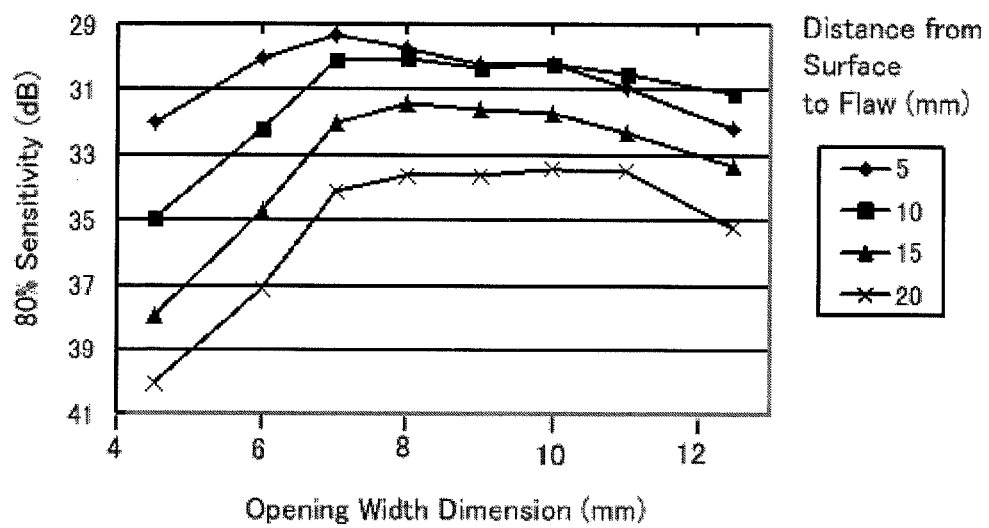
FIGS. 9A and 9B are a data table and a graph showing the intensity of flaw echo at the time when an opening width is changed.

FIGS. 9A and 9B are a data table and a graph showing the intensity of flaw echo at the time when an opening width is changed. FIG. 9A is a data table of 80% sensitivity, and FIG. 9B is a graph of 80% sensitivity. In FIG. 9B, the abscissas represent the opening width, and the ordinates represent the 80% sensitivity. The data in the case where the opening width dimension is 12.5 mm are the data at the time when ultrasonic testing was performed without the installation of the vibration insulating member 4.

In each of data in which the distance from the test object surface to a flaw is different, the value of 80% sensitivity changes depending on the opening width dimension, and has a peak.

Figures 10A, 10B:
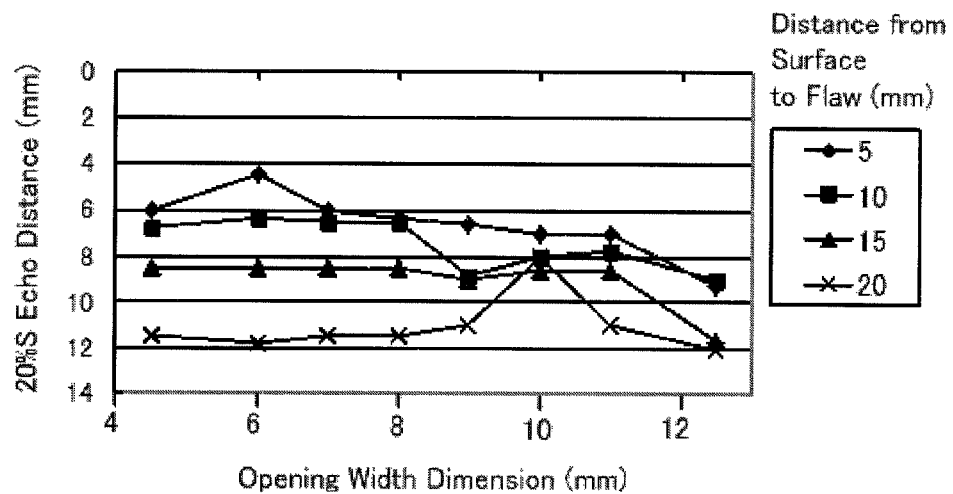
FIGS. 10A and 10B are a data table and a graph showing the range of distance at which surface echo appears at the time when an opening width is changed.

FIGS. 10A and 10B are a data table and a graph showing the range of distance at which surface echo appears at the time when an opening width is changed. FIG. 10A is a data table of 20% S echo distance, and FIG. 10B is a graph of 20% S echo distance. In FIG. 10B, the abscissas represent the opening width, and the ordinates represent the 20% S echo depth.

In the case where the value of 80% sensitivity is in the same degree, the 20% S echo distance has a tendency of being shorter as the opening width dimension decreases.

Based on the above-described data, the opening width dimension corresponding to the distance from the test object surface to the target flaw was determined as described below.

In the case where the distance from the test object surface to the target flaw was 10 mm or shorter, the opening width dimension corresponding to the distance from the test object surface to the target flaw was made an opening width dimension such that the 20% S echo distance was approximately at a minimum, and in the case where the distance from the test object surface to the target flaw exceeded 10 mm, the opening width dimension corresponding to the distance from the test object surface to the target flaw was made an opening width dimension such that the peak intensity of flaw echo was approximately at a maximum, that is, the 80% sensitivity was approximately at a minimum.

From the above-described test results, the opening width dimension corresponding to the distance from the test object surface to the target flaw was set at 6 mm in the case where the distance from the test object surface to the target flaw was 5 mm, was set at 6 mm in the case where the distance from the test object surface to the target flaw was 10 mm, was set at 8 mm in the case where the distance from the test object surface to the target flaw was 15 mm, and was set at 10 mm in the case where the distance from the test object surface to the target flaw was 20 mm.

Ultrasonic testing was performed by installing the vibration insulating member 4 having the opening width dimension corresponding to the distance from the test object surface to the target flaw onto the transducer surface.

By installing the vibration insulating member 4 having the opening width dimension corresponding to the distance from the test object surface to the target flaw onto the transducer surface, the flaw echo of artificial flaw was not buried in surface echo, and the artificial flaw could be detected easily. Therefore, it can be anticipated that even in the ultrasonic testing of natural flaw, even for a flaw near the surface, flaw echo is made less liable to be buried in surface echo, and the flaw can be detected easily.

The present invention is not limited to the configuration of the above-described embodiment, and can be modified variously without departing from the spirit and scope of the present invention.

REFERENCE SIGNS LIST

3 . . . array probe
31 . . . transducer

32 ... array probe body
33 ... transducer surface
4 ... vibration insulating member
41 ... opening part

The invention claimed is:

1. An ultrasonic testing method in which an ultrasonic array probe body having linearly arranged transducers and a transducer surface is used, the method comprising:

providing a specimen having a plurality of artificial flaws, each artificial flaw being at a distance from a surface of the specimen which is different to each of the other artificial flaws;

providing a plurality of vibration insulating members which absorb vibration of the transducer surface, each of the vibration insulating members having an opening part which has a width narrower than a width of the transducer surface, the width of the opening part of each vibration insulating member being different to the width of the opening part of each of the other vibration insulating members, each of the vibration insulating members being arranged over the transducer surface such that a part of the transducer surface in a width direction of the transducer surface is exposed through the opening part and a non-exposed part of the transducer surface is in contact with the insulating member;

performing ultrasonic testing on the specimen using each of the plurality of the vibration insulating members to determine a range of distances from the surface of the specimen in which surface echo appears and to obtain data on an intensity of flaw echo for each artificial flaw for each distance from the surface of the specimen to each artificial flaw and for each of width dimensions of the opening parts of the vibration insulating members, and, based on the obtained data, determining a width dimension of the opening part according to a distance from a surface of a test object to a target flaw located near the surface of the test object;

detachably installing the vibration insulating member having a determined width dimension of the opening part onto the transducer surface of the ultrasonic array probe body; and performing ultrasonic testing on the test object by radiating ultrasonic waves from the transducer surface onto the surface of the test object.

2. An ultrasonic array probe comprising:

an ultrasonic array probe body having transducers linearly arranged and a transducer surface; and a vibration insulating member for absorbing vibrations of the transducer surface, the vibration insulating member having an opening part which has a width narrower than a width of the transducer surface, and being detachably installed onto the transducer surface so that a part of the transducer surface in a width direction of the transducer surface is exposed through the opening part and a non-exposed part of the transducer surface is in contact with the vibration insulating member, wherein a width dimension of the opening part of the insulating member is determined in advance according to a distance from a surface of a test object to a target flaw located near the surface of the test object based on data obtained by performing ultrasonic testing on a specimen using each of a plurality of vibration insulating members, the specimen having a plurality of artificial flaws, each artificial flaw having a different distance from a surface of the specimen, each of the plurality of vibration insulating members having a different width dimension of the opening part, so that the data on a range of distances from the surface of the specimen in which surface echo appears and the data on an intensity of flaw echo for each artificial flaw are obtained for each distance from the surface of the specimen to each artificial flaw and for each width dimension of the opening part of each vibration insulating member.

* * * * *